United States Patent
Pomeranz et al.

[11] Patent Number: 5,882,346
[45] Date of Patent: *Mar. 16, 1999

[54] SHAPABLE CATHETER USING EXCHANGEABLE CORE AND METHOD OF USE

[75] Inventors: Mark L. Pomeranz, Los Gatos; Peter Park, Santa Clara, both of Calif.

[73] Assignee: Cardiac Pathways Corporation, Sunnyvale, Calif.

[*] Notice: This patent issued on a continued prosecution application filed under 37 CFR 1.53(d), and is subject to the twenty year patent term provisions of 35 U.S.C. 154(a)(2).

[21] Appl. No.: 680,426

[22] Filed: Jul. 15, 1996

[51] Int. Cl.$^6$ ..................................................... A61M 25/00
[52] U.S. Cl. .............................. 604/280; 604/49; 604/53; 607/122
[58] Field of Search ..................................... 604/280, 281, 604/282, 283, 264, 49, 51–53, 95, 96, 164; 128/772, 657, 658; 607/122, 119, 116

[56] References Cited

U.S. PATENT DOCUMENTS

| | | | |
|---|---|---|---|
| 4,136,703 | 1/1979 | Wittkampf | 128/419 |
| 4,353,358 | 10/1982 | Emerson | 128/4 |
| 4,738,667 | 4/1988 | Galloway | 604/281 |
| 4,827,941 | 5/1989 | Taylor et al. | 128/772 X |
| 4,898,577 | 2/1990 | Badger et al. | 604/53 |
| 4,917,103 | 4/1990 | Gambale et al. | 604/164 X |
| 4,925,445 | 5/1990 | Sakamoto et al. | 604/95 |
| 4,935,017 | 6/1990 | Sylvanowicz | 604/280 |
| 5,109,830 | 5/1992 | Cho | 128/4 |
| 5,290,229 | 3/1994 | Paskar | 604/95 |
| 5,295,493 | 3/1994 | Radisch, Jr. | 128/772 |
| 5,304,131 | 4/1994 | Paskar | 604/95 |
| 5,354,297 | 10/1994 | Avitall | 606/45 |
| 5,383,852 | 1/1995 | Stevens-Wright | 604/95 |
| 5,391,147 | 2/1995 | Imran et al. | 604/95 |
| 5,427,119 | 6/1995 | Swartz et al. | 128/772 |
| 5,450,842 | 9/1995 | Tovey et al. | 600/206 |
| 5,462,545 | 10/1995 | Wang et al. | 606/41 |
| 5,471,982 | 12/1995 | Edwards et al. | 128/642 |
| 5,487,757 | 1/1996 | Truckai et al. | 607/122 |
| 5,497,774 | 3/1996 | Schwatrz et al. | 128/658 |
| 5,500,012 | 3/1996 | Brucker et al. | 607/122 |
| 5,617,875 | 4/1997 | Schwager | 128/772 |
| 5,628,316 | 5/1997 | Swartz et al. | 128/657 |
| 5,632,734 | 5/1997 | Galel et al. | 604/282 |
| 5,674,197 | 10/1997 | Van Muiden et al. | 604/95 |
| 5,674,271 | 10/1997 | Denker | 607/119 |

FOREIGN PATENT DOCUMENTS

| | | | |
|---|---|---|---|
| 0532109 | 3/1993 | European Pat. Off. | 604/280 |
| 0711573A1 | 5/1996 | European Pat. Off. | |
| 0 715 865 A2 | 6/1996 | European Pat. Off. | |
| PCT/US96/15307 | 4/1997 | WIPO | |

*Primary Examiner*—John D. Yasko
*Attorney, Agent, or Firm*—Limbach & Limbach

[57] ABSTRACT

In a shapable catheter and method for positioning a shapable catheter within a body cavity, a core wire is provided which includes a pre-shaped region bent into a predetermined shape. A catheter is provided which includes a lumen proportioned to slidably receive the core wire. The catheter includes a rigid proximal section and a flexible distal section. During use, the distal end of the catheter is inserted through a patient's vasculature and is passed into a body cavity. The pre-shaped region of the core wire is passed into the lumen and is straightened by the rigid proximal section of the catheter. The pre-shaped region is passed further into the catheter until it reaches the flexible distal region, in which the pre-shaped section re-assumes its predetermined shape and causes the core wire to form the distal section of the catheter into the predetermined shape. The distal section of the catheter is positioned in contact with tissue in the body cavity, and electrodes carried by the distal end are used to map and/or ablate the tissue.

23 Claims, 10 Drawing Sheets

SHAPABLE CATHETER USING EXCHANGEABLE CORE AND METHOD OF USE

FIELD OF THE INVENTION

The present invention relates generally to the field of medical catheters. In particular, the present invention relates to the field of catheters of the type used for mapping electrical activity within the heart and for ablating cardiac tissue.

BACKGROUND OF THE INVENTION

There are a number of conditions in the heart which necessitate monitoring the cardiac tissue for sources of abnormal electrical activity within the heart and/or which require ablation of tissue within the heart where such sources of electrical activity are located.

Two such conditions are atrial fibrillation and ventricular tachycardia. Atrial fibrillation is a condition in the heart in which abnormal electrical signals are generated in the endocardial tissue to cause irregular beating of the heart. One method used to treat atrial fibrillation involves creating several long (i.e. approximately 2–10 cm) lesions on the endocardium within the atria. These lesions are intended to stop the irregular beating of the heart by creating barriers between regions of the atria. These barriers halt the passage through the heart of the abnormal currents generated by the endocardium. This procedure is commonly referred to as the "maze procedure" because it creates a maze of lesions design to block the passage of abnormal currents through the heart.

Existing procedures for forming such linear lesions include the highly invasive technique of opening the patient's chest and heart and forming linear incisions inside the atria. Naturally, the highly invasive nature of this procedure makes it a particularly high risk to the patient and necessitates extraordinarily long recovery time.

Other attempts have been made to form the linear lesions using ablation catheters fed into the heart via the patient's vessels (i.e., the arteries or veins). For example, one such procedure involves inserting into the atria a 7 French catheter having an ablation tip. Radio frequency (RF) energy is supplied to the tip as the tip is dragged across the endocardium, thereby burning linear lesions into the endocardium.

While often successful for forming linear lesions, the ablation tip of the catheter can sometimes lift off of the surface of the endocardium as it is dragged across the endocardium, creating one or more breaks in the lesion. Such breaks minimize the success of the ablation procedure by leaving a path through which current may travel during atrial fibrillation episodes.

Ventricular tachycardia is another condition which generates abnormal electrical activity in the heart and which can require ablation of cardiac tissue associated with the abnormal electrical activity. Ablation of tissue for ventricular tachycardia may be performed using RF energy delivered by an electrode positioned at the tip of an ablation catheter. Typically, the lesions formed by the ablation tip must extend deeply into the tissue and so good contact between the tip electrode and the tissue is important.

In patients experiencing atrial fibrillation and ventricular tachycardia, it is often desirable to map the electrical activity of the cardiac tissue in order to determine the location of the irregular electrical activity so that ablation procedures may be carried out at the appropriate location. One type of mapping catheter utilizes an expandable basket, plaque, helix, coil, or other structure positioned at the distal end of a catheter and a plurality of electrodes carried by the expandable structure.

The expandable structure is initially in a collapsed condition and is fed via the patient's vessels into the chamber of the heart which is to be mapped. Once inside the chamber, the expandable structure is released or moved into its expanded condition and it is positioned such that the electrodes are in contact with the cardiac tissue within the chamber. The electrical activity at each electrode site is monitored and maps showing the electrical activity at various points within the chamber may be produced.

As with ablation procedures, better results are achieved during endocardial mapping procedures if the mapping electrodes are securely supported against the endocardial tissue. If insufficient contact is made between the electrodes and the tissue, the electrical activity of the tissue beneath those electrodes will not be properly recorded.

Procedures and devices for ablating and/or mapping endocardial tissue are therefore desired which utilize catheters having sufficient flexibility and maneuverability to allow introduction of the electrodes into the cardiac chamber with minimal tissue trauma, but which hold the mapping and/or ablation electrodes securely against the target tissue which is to be mapped and/or ablated.

SUMMARY OF THE INVENTION

The present invention is a shapable catheter device which may be used for mapping and/or ablating endocardial tissue or other body tissue or for other medical procedures. The apparatus includes an elongate catheter having a lumen extending longitudinally through it. A core wire is insertable into the catheter via the lumen. The core wire includes a pre-shaped region which is formed of a superelastic material and which is bent into a predetermined shape.

The catheter includes a proximal section which is sufficiently rigid to straighten the core wire when the core wire is disposed within the proximal section. The catheter also includes a distal section which has significantly greater flexibility than the proximal section.

During use, the catheter is introduced into a body cavity such as a cardiac chamber, and the core wire is inserted into the catheter lumen. As the pre-shaped section of the core wire passes through the proximal section of the catheter, the rigidity of the proximal section causes the pre-shaped region of the core wire to straighten. When the pre-shaped region of the core wire enters the flexible distal section of the catheter, the pre-shaped region of the core wire deforms the distal section of the catheter into the predetermined shape.

In the preferred embodiment, electrodes are carried by the distal section of the catheter. During use, these electrodes are positioned in contact with tissue lining the body cavity and are used to ablate the tissue and/or to map the electrical activity of the tissue.

DETAILED DESCRIPTION OF EXEMPLARY EMBODIMENTS

The present invention is comprised generally of a catheter 10 and a pre-shaped core wire 12 which is receivable within the catheter to cause the catheter to form into the shape of the core wire 12.

Figure 1:
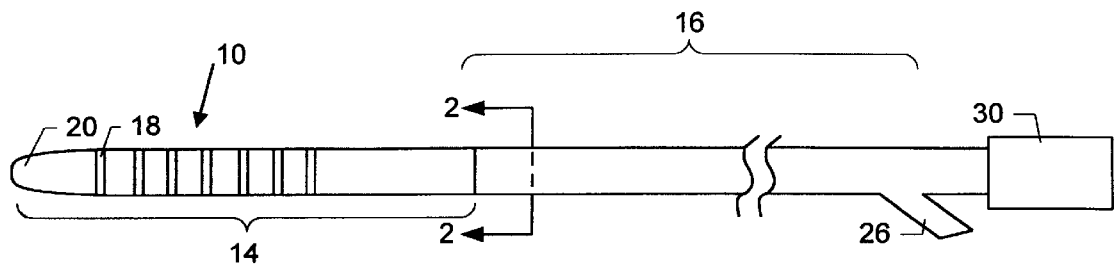
FIG. 1 is a side elevation view of a shapable catheter according to the present invention.

Referring to FIG. 1, the catheter 10 is an elongate shaft having a distal section 14 and a proximal section 16. A plurality of electrodes 18 are mounted to the distal section 14. Electrodes 18 may be conventional ring-type electrodes, or spaced conductive strips or bands formed on the surface of the catheter 10. Alternatively, the electrodes may be provided in combination with a electrolytic solution delivery system as will be described with respect to the embodiment of FIGS. 9–12.

Catheter 10 includes a tip 20 at its distal end. An additional electrode may be mounted to the tip 20.

Figure 2:
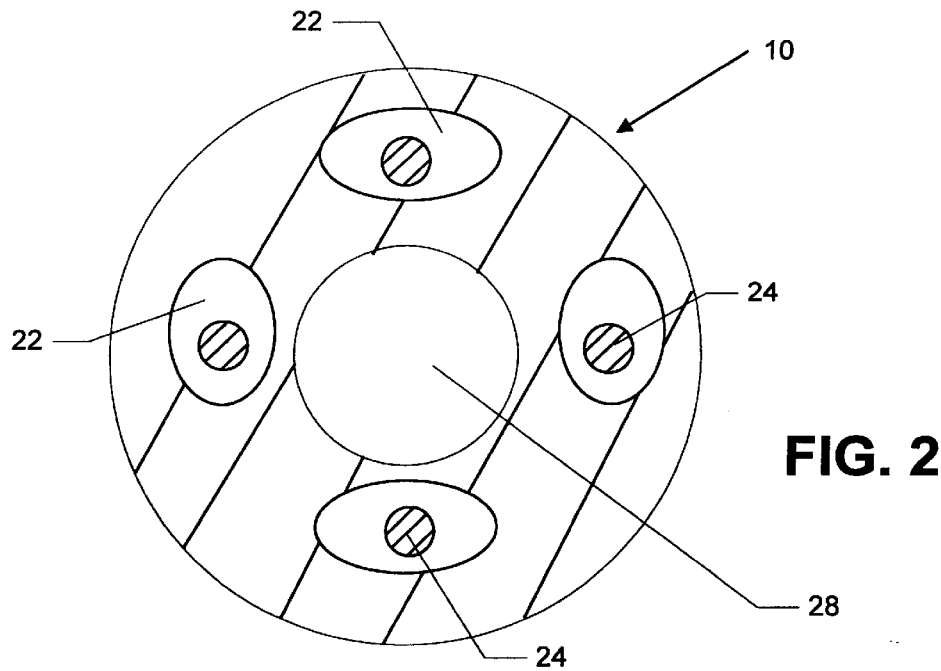
FIG. 2 is a cross-section view of the catheter of FIG. 1, taken along the plane designated 1—1 in FIG. 1.

Referring to FIG. 2, a plurality of lumens 22 extend longitudinally from the distal section 14 of the catheter 10 to the proximal section 16. Lead wires 24, which are electrically coupled to the electrodes 18, extend through the lumens 22 and terminate at an electrical connector 26 (FIG. 1) located at the distal section 14. Connector 26 is attachable to an energy source, such as Model 8002 RF Generator which is available from Cardiac Pathways Corporation, Sunnyvale, Calif., for delivering energy to the electrodes. Connector 26 may alternatively or additionally be connectable to an endocardial mapping system such as Model 8100 Arrhythmia Mapping System available from Cardiac Pathways Corp., Sunnyvale, Calif.

A center lumen 28 also extends longitudinally through the catheter 10, preferably along the central axis of the catheter. During use, the core wire 12 is passed through the center lumen 28 as will be described in detail below. At the catheter's proximal end, center lumen 28 opens into a port 30 through which the core wire 12 is inserted during use.

The center lumen 28 may have a circular crosssection as shown in FIG. 2. Alternatively, both the center lumen 28 and the core wire 12 may have oblong cross-sections (see, for example, core wire 12c and lumen 28a in FIG. 10) to prevent rotation of the core wire within the lumen 28 during use. Such elongate cross-sections are further useful in that they allow for preferential bending of the catheter. In other words, referring to FIG. 10, the oblong cross-section of the catheter 10a allows bending of the catheter to be effectively limited to be across a preferential bending plane, i.e., across long sides 48 of the catheter 10a.

Catheter 10 is preferably constructed of a thermoplastic polymer, polyamid ether, polyurethane or other material having similar properties. A stainless steel braid (not shown) is preferably embedded in the wall of the main shaft by means conventionally known in the art. The inclusion of the braid improves the torque characteristics of the catheter 10 and thus makes the catheter easier to maneuver through a patient's vessels and heart.

The material forming the distal section 14 of the catheter 10 is selected to have a sufficiently low durometer or hardness (e.g., approximately 25–50Shore D) to permit the distal section 14 to be highly flexible. In contrast, the proximal section 16 is formed of a higher durometer material (e.g., approximately 55–80 Shore D) and thus is fairly rigid.

Figure 3A:
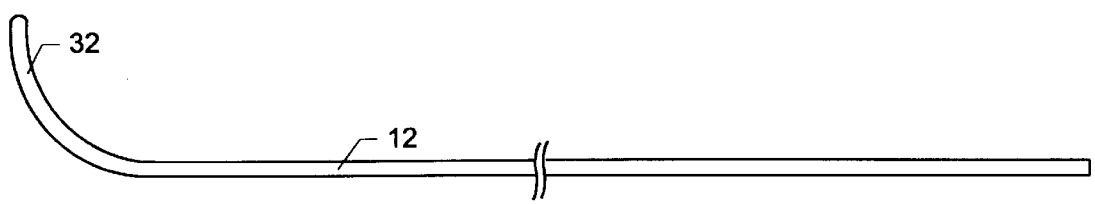
FIGS. 3A, 3B, 4 and 5A are side elevation views of four embodiments of core wires according to the present invention.
Figure 3B:
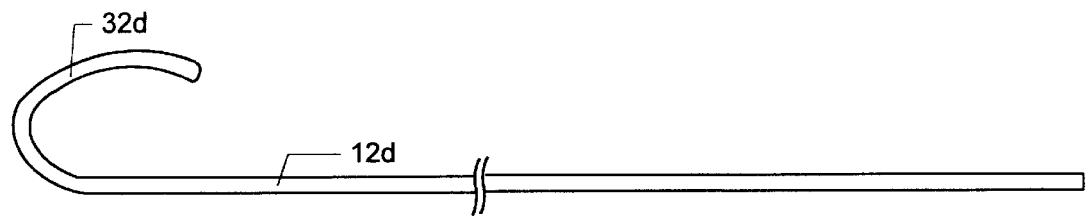
Figure 4:
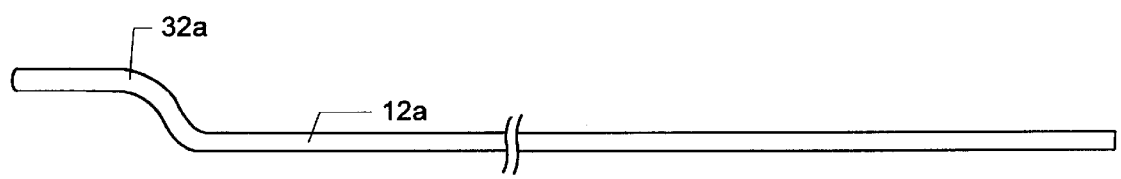
Figure 5B:
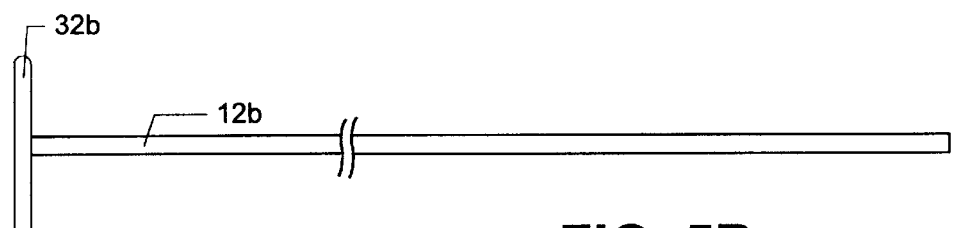
FIG. 5B is an end view of the spiral core wire of FIG. 5A.
Figure 5A:
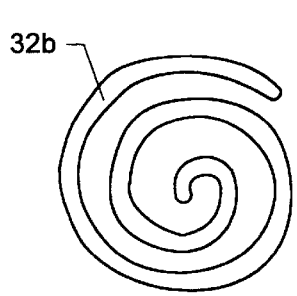

Referring to FIG. 3A, core wire 12 is an elongate wire formed of a superelastic material such as Nitinol. Core wire 12 includes a pre-shaped section 32, preferably at its distal end. The pre-shaped section 32 may have the C-curve shown in FIG. 3A, or it may have one of numerous other shapes including the Z- or S-curve of the core wire 12a of FIG. 4, the spiral shape of the core wire 12b of FIGS. 5A and 5B, or the J-curve of the core wire 12d of FIG. 3B.

Figure 5C:
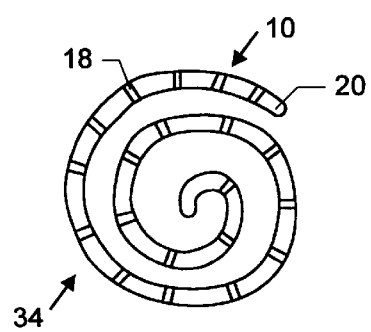
FIG. 5C is an end view of the catheter of FIG. 1 following insertion of the spiral core wire of FIGS. 5A and 5B into the catheter.
Figure 6A:
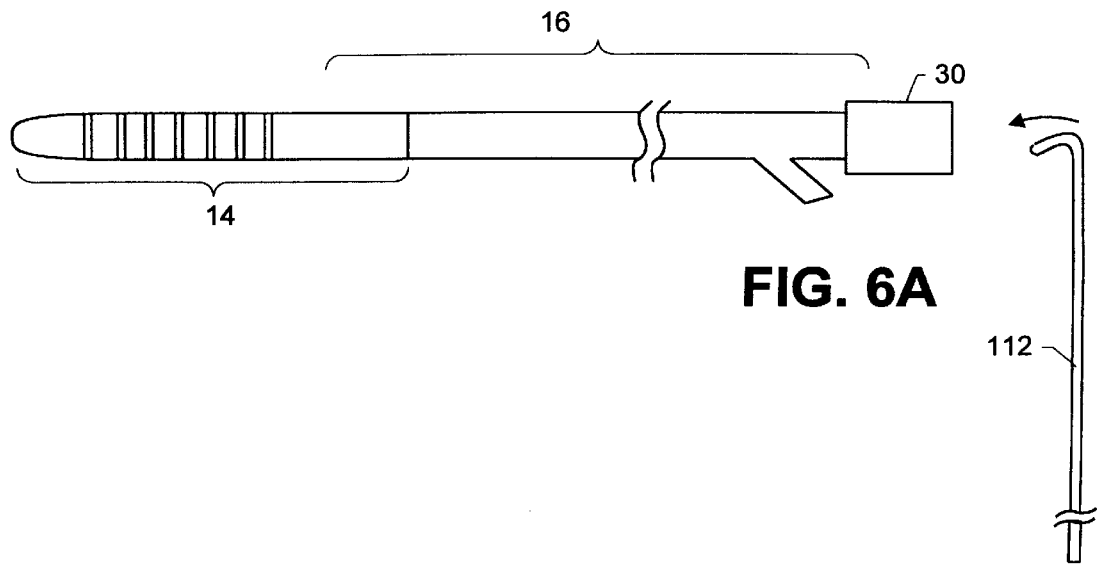
FIGS. 6–7 are a series of side elevation views showing insertion of a core wire according to the present invention into the shapable catheter of FIG. 1.
Figure 6B:
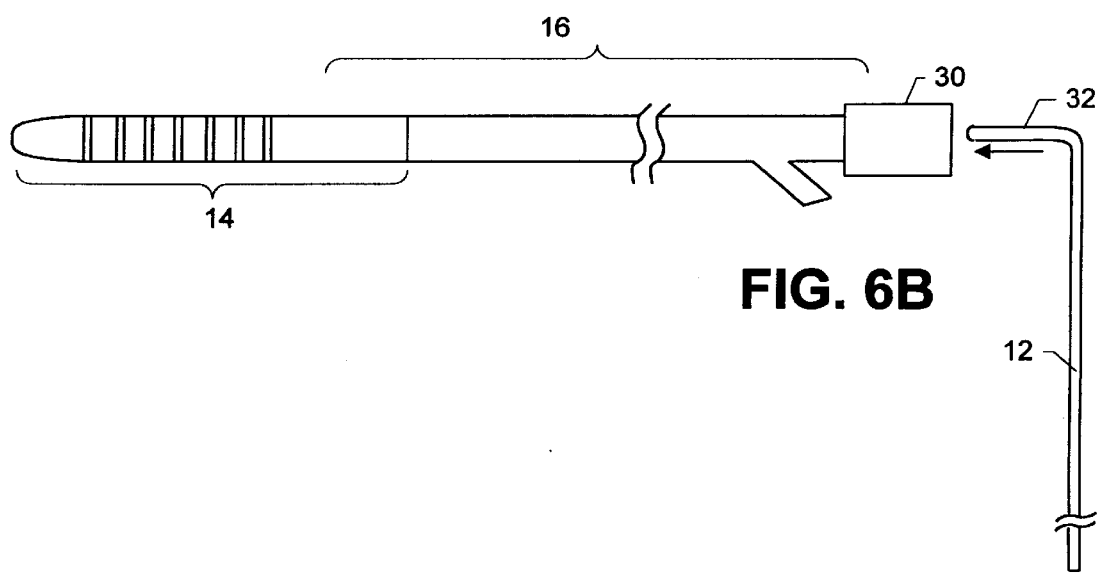
Figure 7:
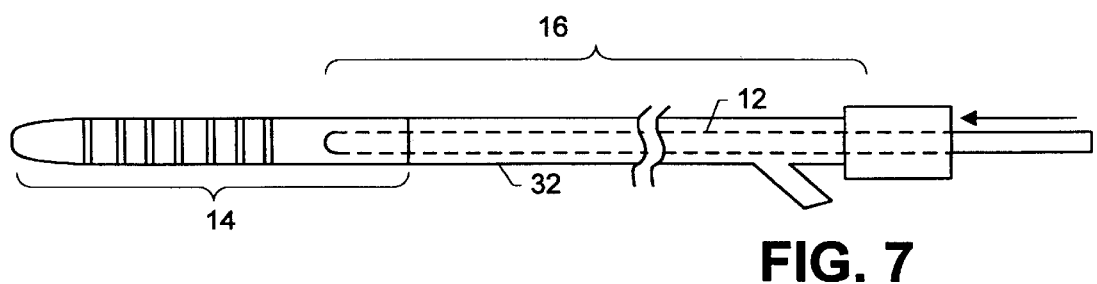
Figure 8A:
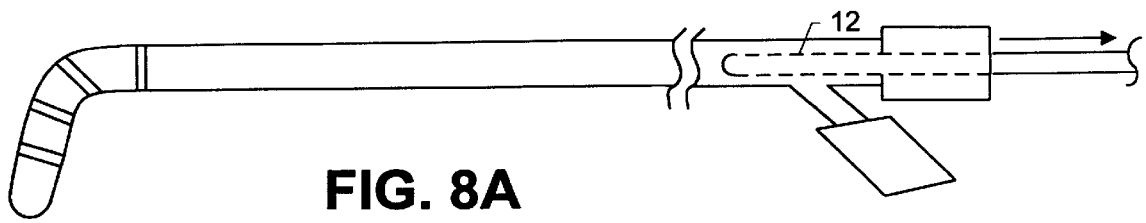
FIG. 8A is a side elevation view showing the catheter of FIGS. 6 and 7 following insertion of the core wire into the catheter.
Figure 8B:
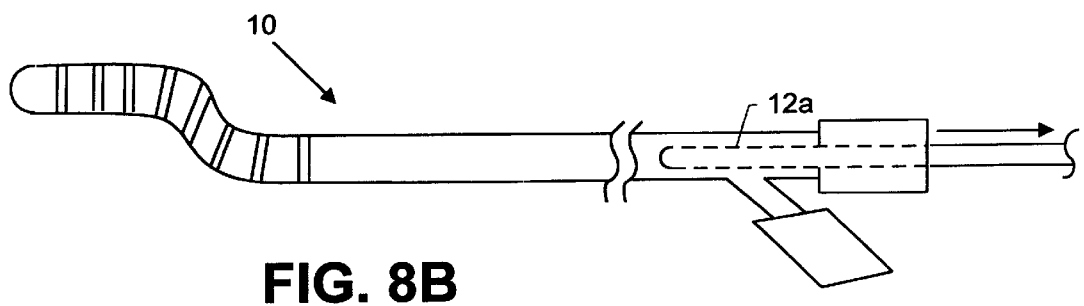
FIG. 8B is a side elevation view showing the catheter of FIGS. 6 and 7 following insertion of the core wire of FIG. 4 into the catheter.

When a core wire such as core wire 12 is introduced into the catheter 10 via port 30 as shown in FIG. 6, core wire 12 is initially straightened by the rigidity of proximal section 16 as illustrated in FIG. 7. As the core wire 12 passes into distal section 14, it is unrestricted by the flexible material of the distal section 14. The characteristics of the superelastic core wire material thus cause the unrestricted core wire to return to its pre-formed shape and to cause the distal section 14 of the catheter 10 to take the shape of the core wire. See, e.g., FIGS. 8A and 5C.

Thus, the shape of the core wire is selected based on its suitability for the procedure for which the catheter 10 is to be used. During use, core wires 12 and 12a (FIGS. 3A, 3B, 4, 8A, and 8B) can cause the catheter 10 to lay along the atrial wall of the heart to create a linear lesion. Spiral core wire 12b (FIGS. 5A and 5B) forms the catheter into a planar mapping plaque (FIG. 5C) which may be positioned into contact with the endocardium for mapping. Innumerable planar or non-planar core wire shapes may be used without exceeding the scope of the present invention.

Use of the shapable catheter 10 according to the present invention will next be described.

First, catheter 10 is inserted through a patient's vasculature to position distal section 14 within the cardiac chamber in which mapping or ablation is to be performed. Introduction of the catheter through the vasculature may be facilitated by first introducing a superelastic guiding core wire, such as core 112 shown in FIG. 6A, into the catheter 10. Guiding core 112 preferably has a small hook 132 at its distal end. This causes the distal portion 14 of the catheter 10 to substantially conform to the shape of the guiding core 112, thereby placing a small bend in the distal end of the catheter. This small bend is useful in preventing the catheter from passing into small side vessels and from catching on structures within the heart during its introduction into the heart.

Once the distal portion 14 of the catheter is situated within the desired chamber of the heart, guiding core 112 is withdrawn. Next, a core wire such as core wire 12 is selected, with the selected core wire shape depending on the region of the heart to be mapped or treated. The selected core wire 12 is inserted into center lumen 28, causing the distal section 14 to assume the pre-formed shape of the core wire 12.

Figure 14:
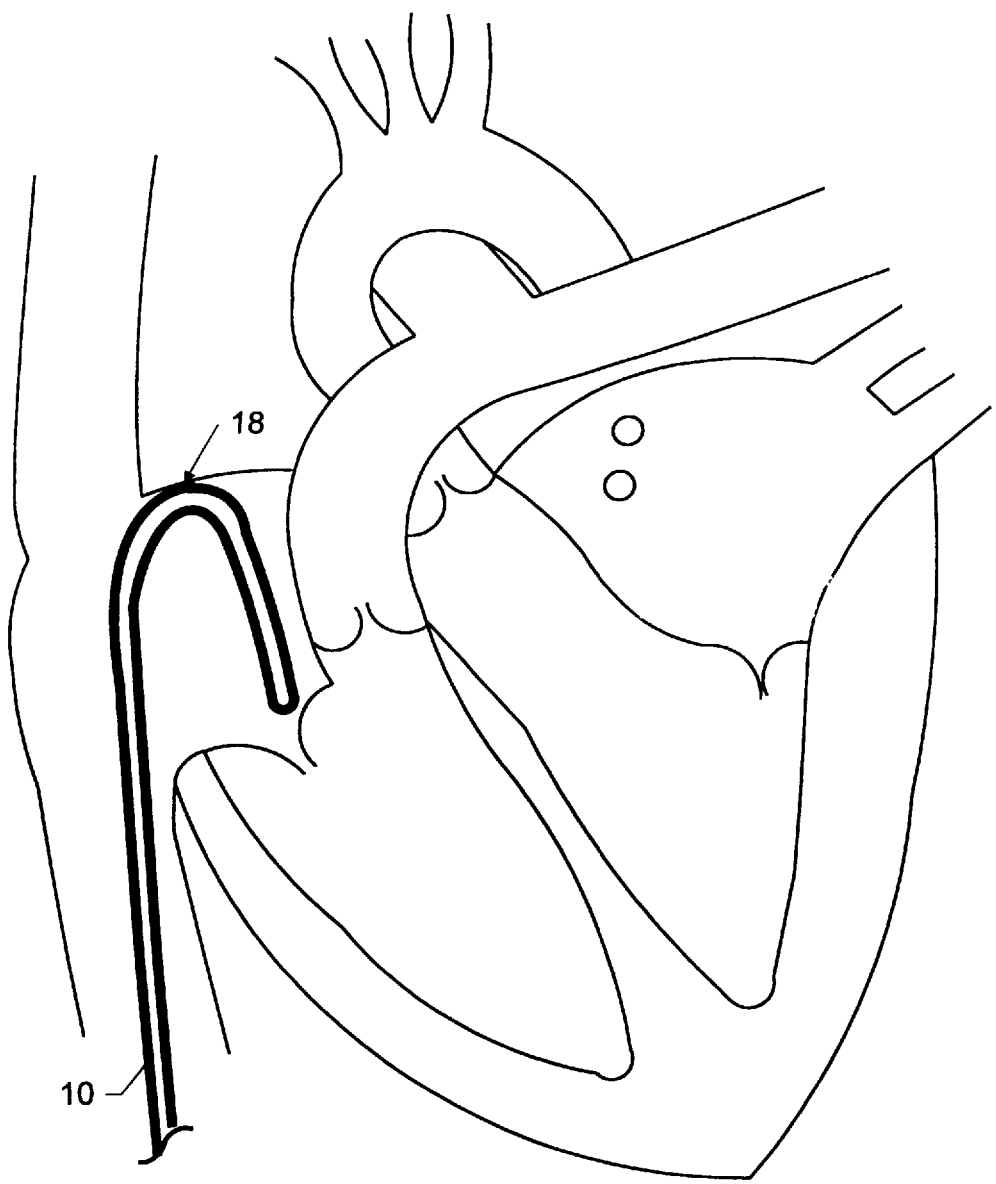
FIG. 14 is a representation of the interior of the heart illustrating the catheter of the present invention when positioned to create a lesion from the superior vena-cava to the tricuspid valve anulus.
Figure 15:
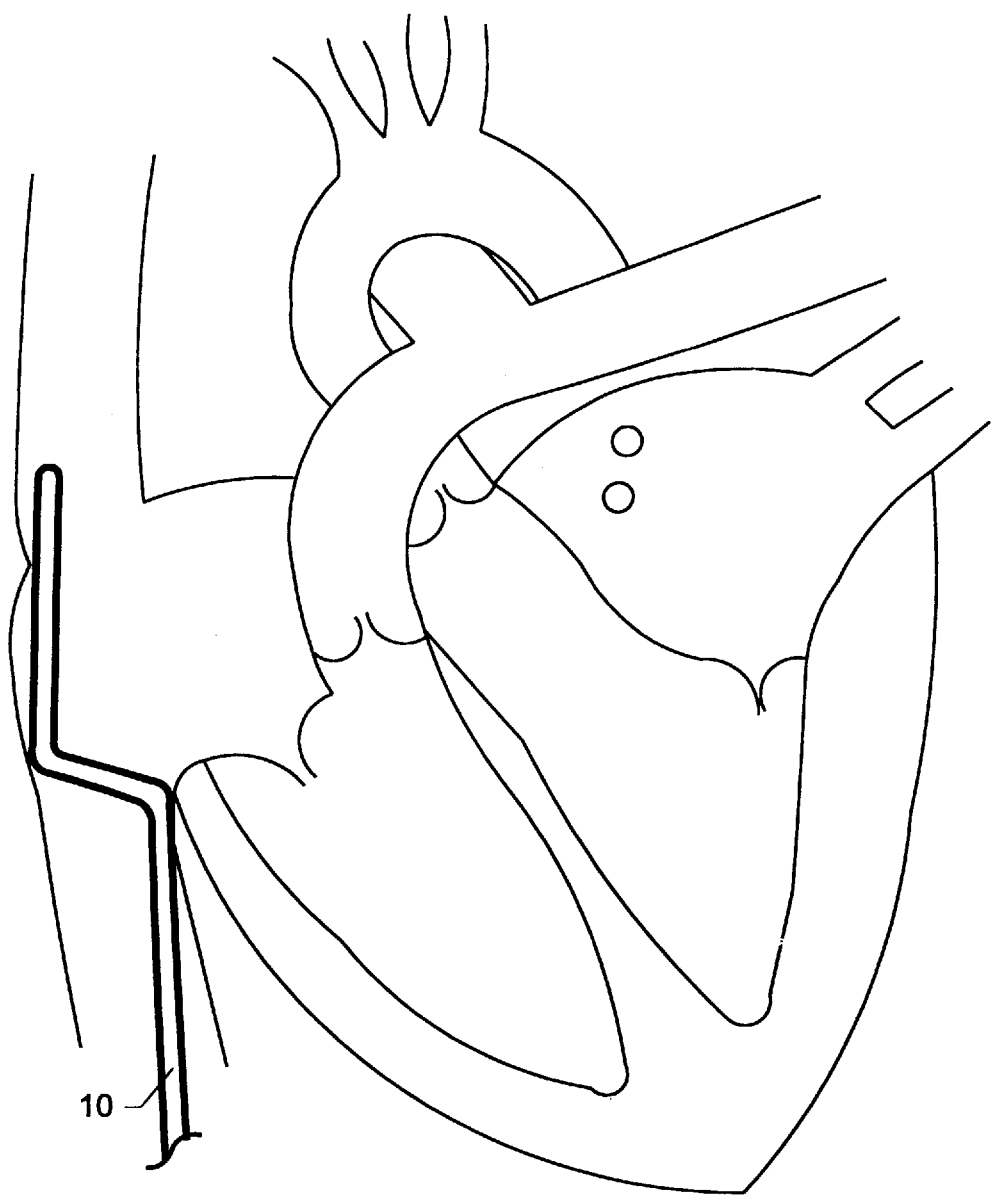
FIG. 15 is a representation of the interior of the heart illustrating the catheter of the present invention when positioned to create a lesion from the inferior vena-cava to the superior vena-cava.
Figure 16:
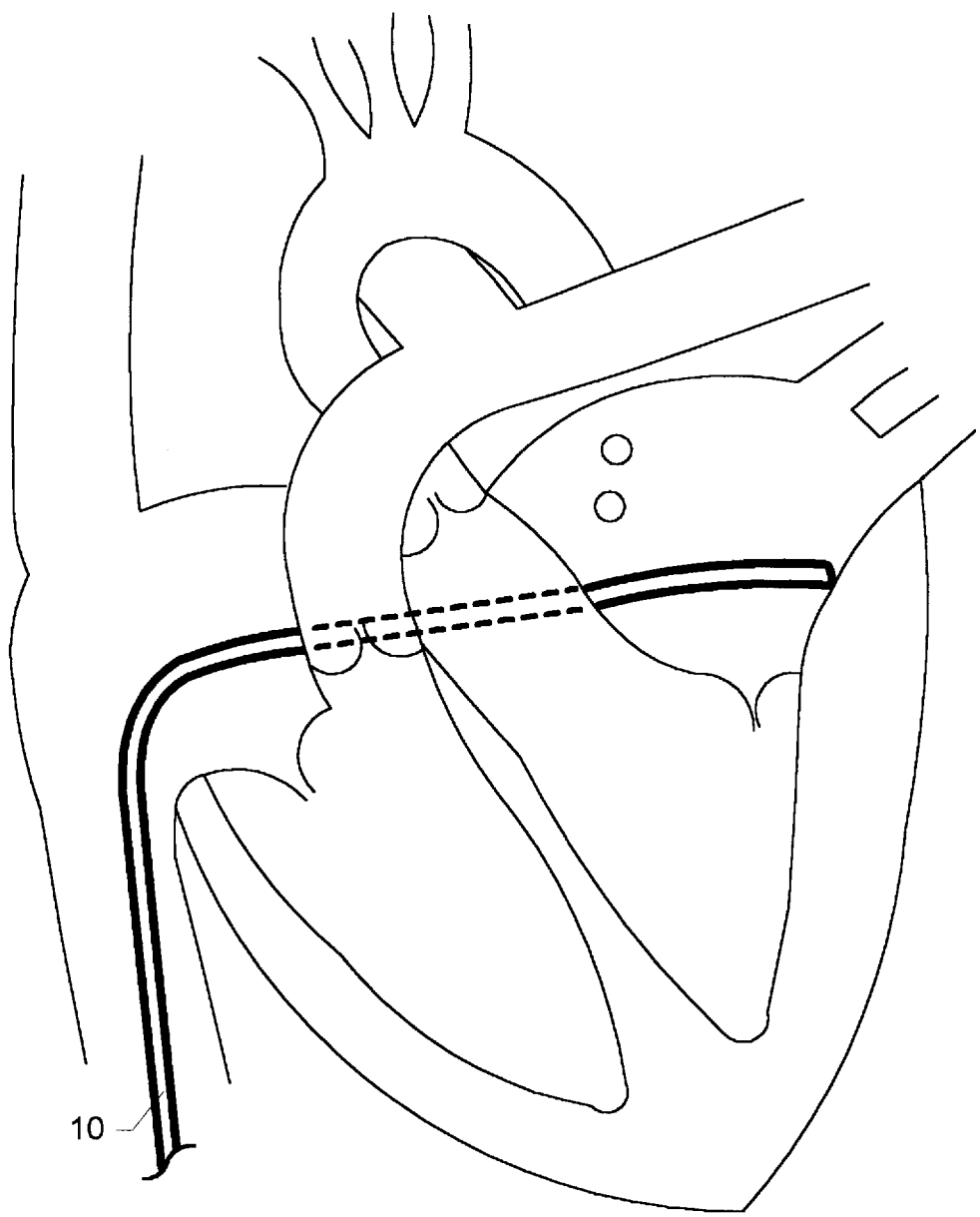
FIG. 16 is a representation of the interior of the heart illustrating the catheter of the present invention when positioned transseptally to create a lesion from the atrial septum to the mitral valve anulus.

The distal section 14 is positioned, preferably under fluoroscopy, against the tissue so that the electrodes 18 make contact with the target cardiac tissue. FIGS. 13–16 illustrate examples of catheter positions within the heart which may be achieved after a selected core wire has been inserted into the catheter and the catheter positioned against the target cardiac tissue. For example, a hook-shaped or J-shaped core wire such as core wire 12d of FIG. 3B may be inserted partially (FIG. 13) or fully (FIG. 14) into the catheter to give the catheter a shape that is useful for forming lesions from the inferior vena-cava to the tricuspid valve anulus (FIG. 13) or from the superior vena-cava to the tricuspid valve anulus (FIG. 14). Alternatively, the core wire 12a of FIG. 4 may be utilized as shown in FIG. 15 to shape the catheter for forming lesions from the inferior vena-cava to the superior vena-cava, or a core having an approximately 90° bend may be utilized as shown in FIG. 16 for creating a lesion from the atrial septum to the mitral valve anulus.

An RF generator and/or a mapping system is connected to the catheter 10 via connector 26, and a mapping and/or ablation procedure is performed.

Once the procedure is completed, the core wire 12 is removed from the catheter 10. The rigid proximal section 16 of the catheter 10 temporarily straightens the core wire 12 into the condition shown in FIG. 7 as the core wire is withdrawn, thus facilitating removal of the core wire.

One significant advantage of the subject invention is that multiple core wires of differing shapes may be used during a single procedure. This allows the physician the ability to change the geometry of the catheter 10 without having to remove the catheter from the heart and to re-insert a new catheter through the patient's vasculature. Instead, the physician may remove first core wire 12 from the catheter 10, as indicated by the arrow in FIG. 8A., following an ablation and/or mapping procedure, and then replace it with a second core wire, such as core wire 12a, as indicated by the arrow in FIG. 8B, to re-shape the catheter 10. The re-shaped catheter 10 is positioned into contact with the endocardium and a second mapping and/or ablation procedure is performed.

Alternative Embodiment

FIGS. 9–12 show an alternative catheter 10a according to the present invention which utilizes an electrode configuration in which an electrolytic solution is used to create a conductive path between the electrodes and the endocardial tissue. This configuration is particularly useful for creating transmural linear lesions during the "maze procedure." Catheters utilizing electrode configurations of this type are described and claimed in pending U.S. application Ser. No. 08/611,656, entitled APPARATUS AND METHOD FOR LINEAR LESION ABLATION, which is incorporated herein by reference.

Figure 9:
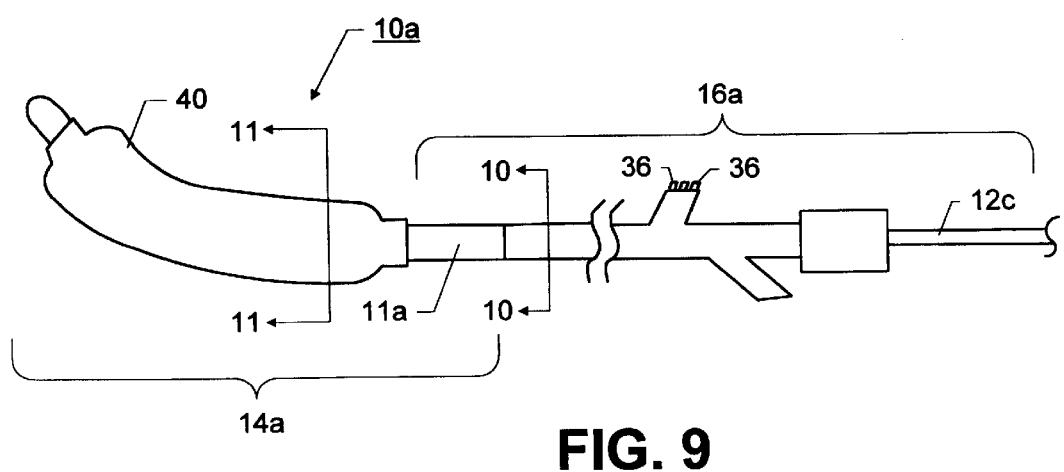
FIG. 9 is a side elevation of an alternative embodiment of a shapable catheter according the present invention, in which an electrolytic solution is used to create a conductive path between the electrodes and the endocardial tissue.
Figure 10:
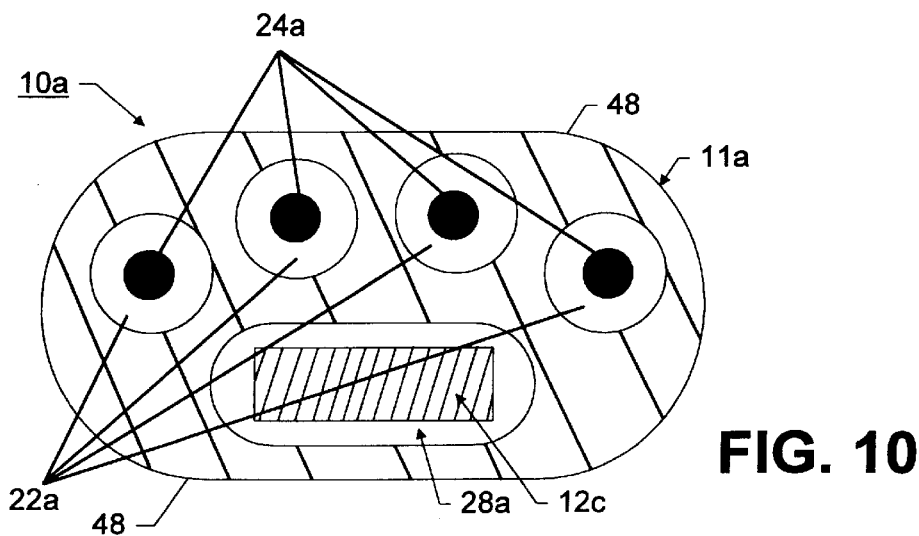
FIG. 10 is a cross-section view of the catheter shaft of the embodiment of FIG. 9, taken along the plane designated 10—10 in FIG. 9.

Referring to FIG. 9, catheter 10a includes distal and proximal sections 14a, 16a which are made of materials similar to those used for the catheter 10 of the embodiment of FIG. 1. Lumens 22a and core wire lumen 28a (FIGS. 10 and 11) extend longitudinally through catheter shaft 11a. The lumen 22a are fluidly coupled to fluid ports 36 (FIG. 9) located at proximal section 16a. A core wire 12c is insertable into the core wire lumen 28a as described with respect to the embodiment of FIG. 1.

Figure 11:
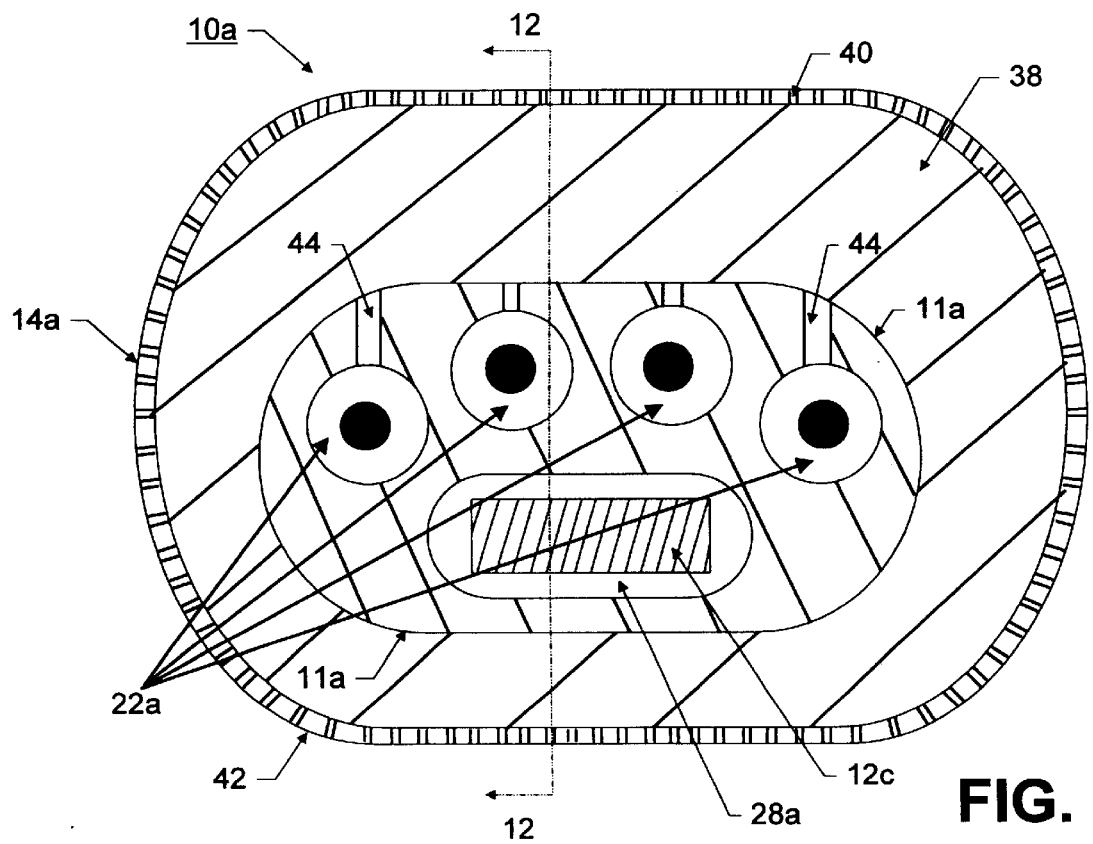
FIG. 11 is a cross-section view of the proximal section of the embodiment of FIG. 9, taken along the plane designated 11—11 in FIG. 9.
Figure 12:
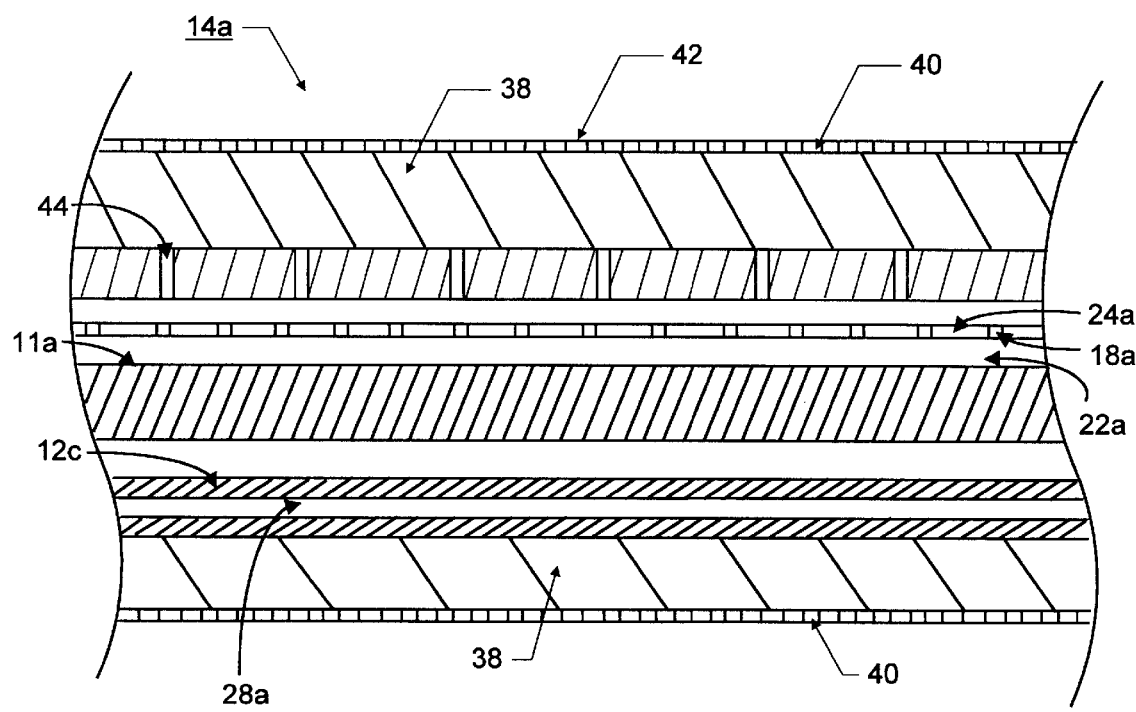
FIG. 12 is a cross-section view of the proximal section of the embodiment of FIG. 9, taken along the plane designated 12—12 in FIG. 11.
Figure 13:
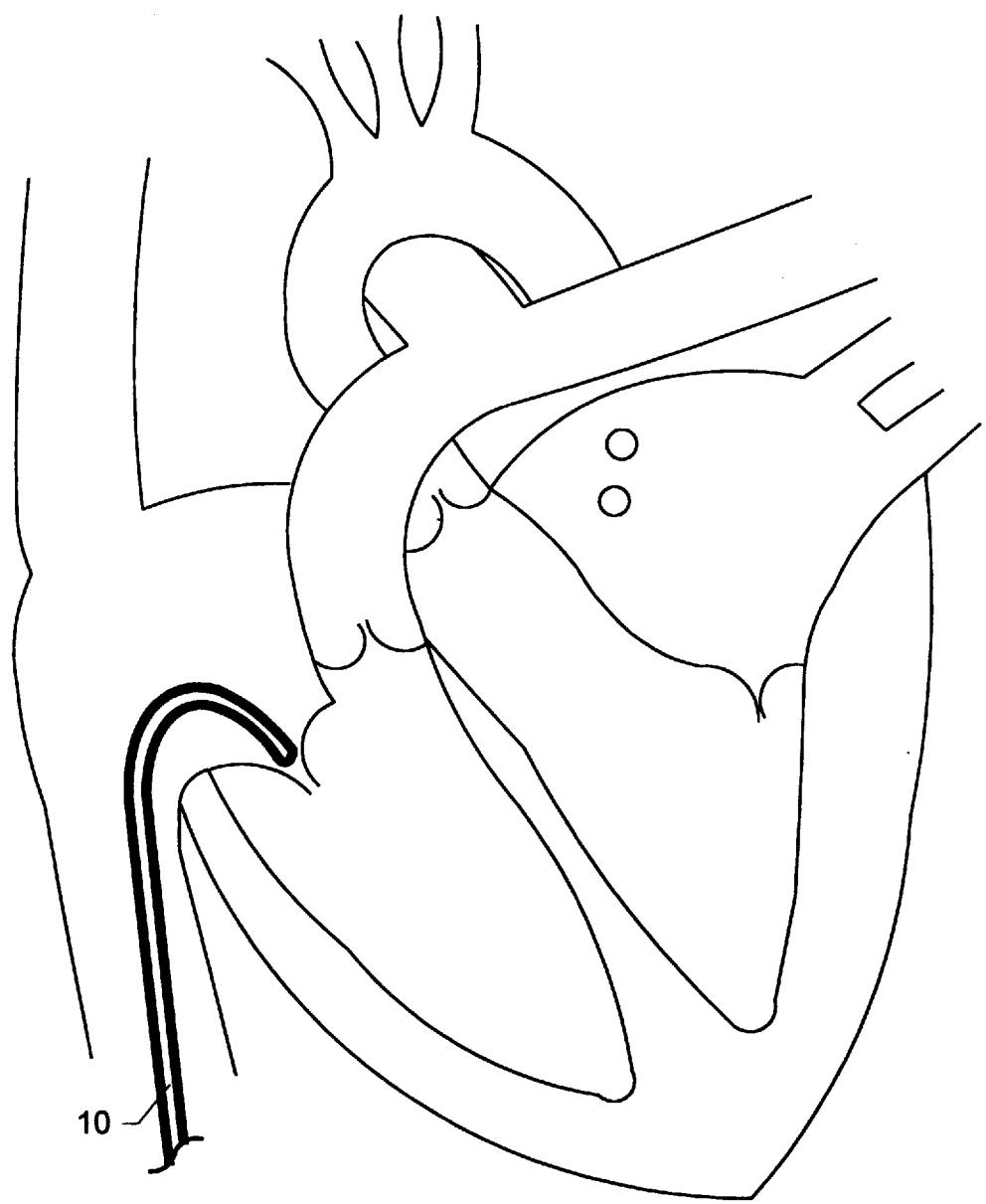
FIG. 13 is a representation of the interior of the heart illustrating the catheter of the present invention when positioned to create a lesion from the inferior vena-cava to the tricuspid valve anulus.

Referring to FIGS. 11 and 12, a deformable member (or "foam layer") 38 is formed in an eccentric configuration at the distal section of catheter 11a such that it is thicker on one side of the catheter 10a than it is on the other side. During use, the side of the distal section having the thick region of foam is positioned against the target tissue which is to be ablated. Foam layer 38 is formed of open cell polyurethane, cotton-like material, open-cell sponge, hydrogels, or other foam-like materials or materials which are permeable by conductive fluids and which exhibit some compressibility. The foam layer need not be segmented but it has been found that RF energy is more effectively channeled to the cardiac tissue by providing the foam in segments rather than in a continuous piece.

Foam layer 38 is enclosed within a fluid impermeable covering 40 which includes a plurality of tiny holes 42. Covering 40 is preferably formed of heat shrink polyethylene, silicone, or other polymeric materials and is preferably held in place by heating its ends to cause the heat shrink material to melt onto the catheter shaft. Covering 40 may also be a dip coating formed on the foam surface.

Holes 42 in the covering 40 may be formed only in the side of the covering at which the foam 38 is thickest. This helps to focus the RF energy onto the target tissue within the heart.

Holes 44 extend from fluid lumen 22a through the catheter shaft 11a to the foam layer 38. The holes 44 are located at the side of the catheter 10a at which the thickened foam region is located to permit the flow of conductive fluid from the fluid lumen 22a to the foam 38 and then through the holes 40 in the covering.

Rather than utilizing ring electrodes of the type described above, the alternative embodiment utilizes conductive wires 24a or flat conductive ribbons, each of which is covered by an insulated coating. Exposed electrode regions 18a (FIG. 12) that are stripped of insulative material are spaced along the portion of the wires 24a that is located within the distal section 14a.

During use, the distal section of the catheter 10a is positioned adjacent to the body tissue which is to be ablated. RF energy is delivered to the electrodes while saline or other conductive fluid is simultaneously delivered through the lumen 22a. The conductive fluid passes the electrodes 18a within the lumen 22a. It further flows via holes 44 through the foam 38 and through the holes 42 in the covering into contact with the body tissue, thereby improving the coupling of the RF energy from the electrodes to the tissue and improving the efficiency of the ablation of the tissue. Use of the shapable aspects of the catheter 10a is the same as that described with respect to the catheter 10a of FIG. 1 and need not be repeated.

Two embodiments of shapable catheters and three embodiments of shapable catheter core wires have been described herein. It should be appreciated, however, that these embodiments have been given by way as example and are not intended to limit the scope of the appended claims. Moreover, although mapping and ablation have been given as exemplary applications of the present invention, the scope of the present invention is not limited to those applications, as the shapable catheter described herein is suitable for use in other medical applications as well.

What is claimed is:

1. A shapable medical apparatus comprising, in combination:
   a core wire having a distal portion with a predetermined non-linear shape; and
   a catheter having a lumen proportioned to slidably receive the core wire, the catheter including a proximal section and a distal section, the distal section having greater flexibility than the proximal section, the core wire slidably receivable within the lumen such that when the core wire is introduced into the proximal section of the catheter, said distal portion is substantially straightened by the proximal section of the catheter, and when said core wire is advanced so that at least a portion of the distal portion is within the distal section of the catheter, the catheter is deformed to approximate the non-linear shape of the portion of the distal portion of the core wire that is within the distal section.

2. The apparatus of claim 1 wherein the predetermined shape is a spiral.

3. The apparatus of claim 1 wherein the predetermined shape is an approximate Z-curve.

4. The apparatus of claim 1 wherein the predetermined shape is an approximate C-curve.

5. The apparatus of claim 1 wherein the predetermined shape is an approximate J-curve.

6. The apparatus of claim 1 wherein the catheter and core wire are configured for preferential bending across a preferential bend plane.

7. The apparatus of claim 6 wherein the catheter has an elongate cross-section.

8. The apparatus of claim 1 wherein the core wire is formed of a superelastic material.

9. The apparatus of claim 8 wherein the superelastic material is Nitinol.

10. A method of positioning a catheter within a body cavity comprising the steps of:
   (a) providing a core wire including a distal portion having a predetermined non-linear shape and further providing a catheter having a lumen proportioned to slidably receive the core wire, wherein the catheter includes a proximal section and a distal section, the distal section having greater flexibility than the proximal section;
   (b) passing the catheter through a vessel and into a body cavity;
   (c) inserting the distal portion of the core wire into the lumen;
   (d) passing the distal portion of the core wire through the proximal section of the catheter, causing the distal portion of the core wire to substantially straighten; and
   (e) passing at least a portion of the distal portion of the core wire into the distal section of the catheter, causing the portion of the distal portion of the core wire to deform the distal section of the catheter to approximate the non-linear shape of the portion of the distal portion that is within the distal section of the catheter.

11. The method of claim 10 further comprising the steps of:
   (f) withdrawing the core wire from the catheter distal section into the catheter proximal section, causing the core wire to substantially straighten;
   (g) withdrawing the core wire from the lumen; and
   (h) after step (g), withdrawing the catheter from the body cavity.

12. The method of claim 10 wherein:
   step (a) includes the step of providing a guiding core wire having a distal portion; and
   step (b) includes the step of inserting the distal portion of the guiding core wire into the lumen and, after passing the catheter into the body cavity, withdrawings the guiding core wire from the lumen.

13. A shapable medical apparatus comprising, in combination:
   a core wire having a distal portion with a predetermined non-linear shape;
   a catheter having a lumen proportioned to slidably receive the core wire, the catheter including a proximal section and a distal section, the distal section having greater flexibility than the proximal section, the core wire slidably receivable within the lumen such that when the core wire is introduced into the proximal section of the catheter, said distal portion is substantially straightened by the proximal section of the catheter, and when said core wire is advanced so that at least a portion of the distal portion is within the distal section of the catheter, the catheter is deformed to approximate the non-linear shape of the portion of the distal portion of the core wire that is within the distal section; and
   a plurality of electrodes mounted on the distal section of the catheter.

14. A shapable medical apparatus comprising, in combination:
   a first core wire having a distal portion with a predetermined non-linear shape;
   a second core wire having a distal portion with a second predetermined non-linear shape, the second predetermined shape being different from the predetermined shape of the first core wire; and
   a catheter having a lumen proportioned to slidably receive the core wires, the catheter including a proximal section and a distal section, the distal section having greater flexibility than the proximal section, each core wire slidably receivable within the lumen such that when one of the core wires is introduced into the proximal section of the catheter, said distal portion is substantially straightened by the proximal section of the catheter, and when said core wire is advanced so that at least a portion of the distal portion is within the distal section of the catheter, the catheter is deformed to approximate the non-linear shape of the portion of the distal portion of the core wire that is within the distal section.

15. A method of positioning a catheter within a body cavity comprising the steps of:
   (a) providing a core wire including a distal portion having a predetermined non-linear shape and further providing a catheter having a lumen proportioned to slidably receive the core wire, wherein the catheter includes a proximal section and a distal section, the distal section having greater flexibility than the proximal section;

(b) passing the catheter through a vessel and into a body cavity;

(c) inserting the distal portion of the core wire into the lumen;

(d) passing the distal portion of the core wire through the proximal section of the catheter, causing the distal portion of the core wire to substantially straighten;

(e) passing at least a portion of the distal portion of the core wire into the distal section of the catheter, causing the portion of the distal portion of the core wire to deform the distal section of the catheter to approximate the non-linear shape of the portion of the distal portion that is within the distal section of the catheter;

(f) removing the core wire from the catheter;

(g) providing a second core wire, the second core wire including a second distal portion having a second predetermined non-linear shape;

(h) inserting the second distal portion of the second core wire into the lumen;

(i) passing the second distal portion through the proximal section of the catheter, causing the second core wire to substantially straighten; and (j) passing at least a portion of the second distal portion of the second core wire into the distal section of the catheter, causing the distal section of the catheter to deform to approximate the non-linear shape of the portion of the second distal portion that is within the distal section of the catheter.

16. A method of positioning a catheter within a body cavity comprising the steps of:

(a) providing a core wire including a distal portion having a predetermined non-linear shape and further providing a catheter having a lumen proportioned to slidably receive the core wire, wherein the catheter includes a proximal section and a distal section, the distal section having greater flexibility than the proximal section, and further providing electrodes on the distal section of the catheter;

(b) passing the catheter through a vessel and into a body cavity;

(c) inserting the distal portion of the core wire into the lumen;

(d) passing the distal portion of the core wire through the proximal section of the catheter, causing the distal portion of the core wire to substantially straighten;

(e) passing at least a portion of the distal portion of the core wire into the distal section of the catheter, causing the portion of the distal portion of the core wire to deform the distal section of the catheter to approximate the non-linear shape of the portion of the distal portion that is within the distal section of the catheter;

(f) positioning the electrodes into contact with tissue in the body cavity; and (g) delivering RF energy to the electrodes to ablate the tissue.

17. A method of positioning a catheter within a body cavity comprising the steps of:

(a) providing a core wire including a distal portion having a predetermined non-linear shape and further providing a catheter having a lumen proportioned to slidably receive the core wire, wherein the catheter includes a proximal section and a distal section, the distal section having greater flexibility than the proximal section, and further providing electrodes on the distal section of the catheter;

(b) passing the catheter through a vessel and into a body cavity;

(c) inserting the distal portion of the core wire into the lumen;

(d) passing the distal portion of the core wire through the proximal section of the catheter, causing the distal portion of the core wire to substantially straighten;

(e) passing at least a portion of the distal portion of the core wire into the distal section of the catheter, causing the portion of the distal portion of the core wire to deform the distal section of the catheter to approximate the non-linear shape of the portion of the distal portion that is within the distal section of the catheter;

(f) positioning the electrodes into contact with tissue in the body cavity; and (g) using the electrode to detect electrical activity of the tissue.

18. A shapable medical apparatus comprising, in combination:

a core wire having a distal portion with a predetermined non-linear shape;

a catheter having a lumen proportioned to slidably receive the core wire, the catheter including a proximal section and a distal section, the distal section having greater flexibility than the proximal section, the core wire slidably receivable within the lumen such that when the core wire is introduced into the proximal section of the catheter, said distal portion is substantially straightened by the proximal section of the catheter, and when said core wire is advanced so that at least a portion of the distal portion is within the distal section of the catheter, the catheter is deformed to approximate the non-linear shape of the portion of the distal portion of the core wire that is within the distal section;

a source of ablation energy;

an ablation section on the distal section of the catheter, the ablation section including at least one electrode coupled to the source of ablation energy, and a fluid port for delivering conductive fluid into contact with the electrodes and to cause said fluid to create a conductive path between the electrodes and the tissue when the electrodes are positioned adjacent body tissue.

19. The apparatus of claim 18 wherein the ablation section further includes a fluid permeable deformable member at least partially covering the electrodes.

20. The apparatus of claim 19 wherein the deformable member includes a layer of foam material formed over the electrodes.

21. The apparatus of claim 19, further comprising a covering on the deformable member, the covering formed of a material substantially impermeable to fluid, the covering including at least one opening sized to allow passage of fluid out of the covering.

22. The apparatus of claim 18 wherein the ablation section further includes electrodes configured to measure electrical activity of adjacent body tissue.

23. The apparatus of claim 15 further comprising the steps of:

after steps (e) and (j), positioning the catheter in a desired location within the body and using it to gather diagnostic information and/or to deliver therapy to adjacent tissue.

* * * * *